(12) United States Patent
Bogdanovich (10) Patent No.: US 11,293,788 B2
(45) Date of Patent: Apr. 5, 2022

(54) SUPER MODULAR MONITORING SYSTEM

(71) Applicant: Cipher Skin, Denver, CO (US)

(72) Inventor: Phillip Bogdanovich, Evergreen, CO (US)

(73) Assignee: Cipher Skin, Denver, CO (US)

( * ) Notice: Subject to any disclaimer, the term of this patent is extended or adjusted under 35 U.S.C. 154(b) by 0 days.

(21) Appl. No.: 16/834,821

(22) Filed: Mar. 30, 2020

(65) Prior Publication Data

US 2021/0190556 A1    Jun. 24, 2021

Related U.S. Application Data

(60) Provisional application No. 62/953,309, filed on Dec. 24, 2019.

(51) Int. Cl.

| | | |
|---|---|---|
| *G01D 11/30* | (2006.01) | |
| *G01D 21/02* | (2006.01) | |
| *A61B 5/0205* | (2006.01) | |
| *A61B 5/00* | (2006.01) | |
| *G01M 5/00* | (2006.01) | |

(52) U.S. Cl.
CPC .............. *G01D 11/30* (2013.01); *G01D 21/02* (2013.01); *A61B 5/0205* (2013.01); *A61B 5/6804* (2013.01); *A61B 2562/066* (2013.01); *G01M 5/0025* (2013.01)

(58) Field of Classification Search
CPC .................................. G01L 1/22; A61B 5/00
See application file for complete search history.

(56) References Cited

U.S. PATENT DOCUMENTS

| | | | |
|---|---|---|---|
| 10,542,934 B2* | 1/2020 | Bogdanovich | A61B 5/1116 |
| 10,903,415 B2* | 1/2021 | Dardona | H01L 27/20 |
| 2015/0102942 A1 | 4/2015 | Houser et al. | |
| 2015/0366504 A1* | 12/2015 | Connor | A61B 5/6804 |
| | | | 600/301 |
| 2017/0153105 A1 | 6/2017 | Chang et al. | |
| 2018/0184735 A1 | 7/2018 | Longinotti-Buitoni et al. | |
| 2019/0046114 A1* | 2/2019 | Bogdanovich | A61B 5/6805 |
| 2020/0300718 A1* | 9/2020 | Bogdanovich | H05K 1/038 |

* cited by examiner

*Primary Examiner* — Jamel E Williams
(74) *Attorney, Agent, or Firm* — LKGlobal | Lorenz & Kopf, LLP (57) ABSTRACT

A super modular monitoring system is disclosed. The system may include a lattice having a plurality of intersections, and which may be formed of a flexible conductive material having a shape comprising repeating geometric patterns. The lattice of the system may serve as the primary sensor of the super modular monitoring system. The system may also include any number of secondary sensors with each being disposed at an intersection of the plurality of intersections of the lattice. The secondary sensors may be in electrical communication with the primary sensor, which may include transmission of both power and data. The system may further include a monitoring system in electrical communication with the lattice. One or more lattices of the system may be coupled together to form a super lattice. The primary and secondary sensors may transmit data simultaneously to the monitoring system for further analysis.

12 Claims, 8 Drawing Sheets

FIG. 8

SUPER MODULAR MONITORING SYSTEM

CROSS-REFERENCE TO RELATED APPLICATIONS

This application claims priority to U.S. Provisional Application Ser. No. 62/953,309, filed Dec. 24, 2019, the entire contents of which is incorporated herein by reference.

FIELD OF THE INVENTION

The present application relates to sensor technologies, monitoring technologies, data analysis technologies, power and data transmission technologies, and, more particularly, to a super modular monitoring system and an accompanying method for utilizing the super modular monitoring system.

BACKGROUND

Prior art monitoring systems require the design of specific circuitry for each sensor or array of sensors. Thus, if the monitoring needs change, an entirely new sensor system must be designed. This is both costly and time-consuming. Moreover, because each sensor in prior art systems transmits data individually, the monitoring system must process the data before it can report on the condition of the object being monitored. This causes a delay in reporting as well as introduces potential error in the measurements. Another potential problem occurs if one or more sensors does not transmit data for a certain timeframe. This may cause "holes" in the data which may reduce the accuracy of the monitoring system's report. Thus, current sensor monitoring systems are expensive, time consuming to design, require significant data processing, and may not be accurate. Based on the foregoing, current technologies and processes may be modified and improved so as to provide enhanced functionality and features for users and systems. Such modifications and improvements may be utilized to enhance monitoring of objects, analyze data associated with the monitoring, determine conditions associated with monitored objects, among other functionality and features. Such enhancements and improvements may provide for improved user satisfaction, increased reliability, increased functionality, increased access to higher-quality data, among other benefits.

SUMMARY

The present disclosure relates to using a monitoring system, and in particular a monitoring system being made of a lattice forming a sensors-within-a-sensor configuration where some or all of the sensors may be electrically connected to one another. The primary sensor/lattice may transmit both power and data concurrently to collect information. The use of such a lattice allows for super modularity of the monitoring system because sensors may be removed and replaced within the lattice without redesigning the circuitry of the monitoring system. Additional lattices may also be added to the monitoring system to cover additional surface area or introduce additional monitoring capabilities.

The present disclosure provides a modular monitoring system that allows a user to monitor an object, such as a 3D object, using a series of lattices. The use of lattices allows the monitoring system to be modular—i.e. new sensors and/or lattices may be added or subtracted from the system as needed. Thus, the monitoring system may be adapted to changes in size, shape, or type of monitoring needed without redesigning the system or adding circuits. Additionally, the present disclosure includes multiple sensors capable of measuring multiple types of conditions. Because all of these sensors may be on the same lattice, all of the data from the sensors may be sent to the monitoring system at the same time over the same transmission lines. This reduces the amount of data processing necessary and improves the speed and accuracy of reporting. Because all of the sensors send data at the same time, there are no "holes" in the data.

A system including a lattice having a plurality of intersections is disclosed. The lattice may be formed of a flexible conductive material having a shape comprising repeating geometric patterns, and the lattice may be a primary sensor. The system also includes a secondary sensor disposed at one of the intersections of the plurality of intersections of the lattice. In certain embodiments, the secondary sensor may be configured to be in electrical communication with the primary sensor. Electrical communication may include the transmission of both power and data. The system may further include a monitoring system in electrical communication with the lattice. In certain embodiments, one or more lattices may be coupled together to form a super lattice. In certain embodiments, a plurality of additional secondary sensors may be disposed at other intersections of the plurality of intersections of the lattice and/or super lattice. The primary and secondary sensors may both be configured to transmit data associated with the object and/or an environment associated with the object to the monitoring system at the same time through the lattice. However, in certain embodiments, the primary and secondary sensors may be configured to transmit data to the monitoring system at different times, staggered times, and/or any other desired time intervals.

A method for monitoring an object with a sensor-within-a-sensor system includes approximating a surface area of the object, determining an area of interest upon the surface area, providing a lattice formed of a flexible conductive material having a shape comprising repeating geometric patterns to cover the area of interest, connecting the lattice to a monitoring system, sensing a first condition associated with the object by using the lattice, providing a secondary sensor at an intersection of the plurality of intersections of the lattice to monitor a second condition, and transmitting the first and the second conditions to the monitoring system at a same time. The lattice may have a plurality of intersections and is capable of conducting power and data signals. The monitoring system may be configured to receive the power and data signals. A plurality of lattices may be provided to monitor the area of interest. The secondary sensor may be replaced with a replacement secondary sensor. The lattice may be removed and replaced with a replacement lattice. The lattice may monitor a first condition by monitoring the voltage within the lattice.

A system includes a primary sensor formed of a conductive material provided in repeating geometric shapes. The repeating geometric shapes may include a plurality of intersections of the conductive material. The system also includes a secondary sensor positioned at one of the intersections of the primary sensor. The secondary sensor may be connected to the primary sensor through the conductive material. The conductive material may be flexible and transmit both power and data signals. The system may also include a monitoring system that receives signals from the primary and secondary sensors. The monitoring system may receive data signals from the primary and secondary sensors on the same system clock. A plurality of secondary sensors may be positioned at a plurality of intersections. A plurality of primary sensors may be connected to one another. The secondary sensors may be primarily formed of gold foil. The system may be used to monitor at least two conditions of at least a portion of an object, including oil pipelines and the human body.

DETAILED DESCRIPTION

Figure 1:
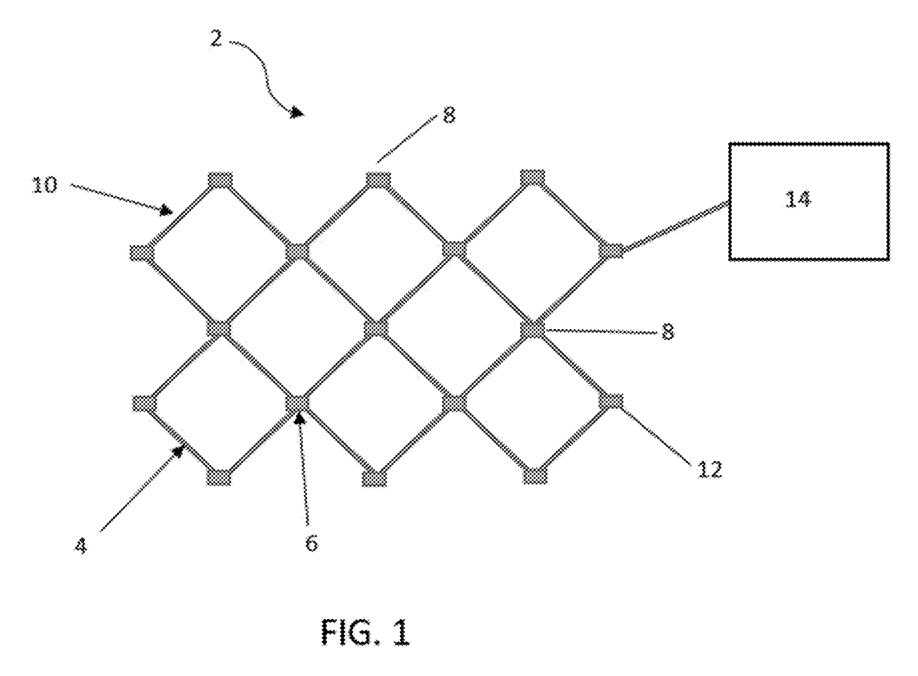
FIG. 1 is an overhead view one lattice of the Super Modular Monitoring System.

As shown in FIG. 1, a Super Modular Monitoring System 2 may be made up of at least one lattice 4, lattice intersections 6, a primary sensor 10, secondary sensors 12, and a monitoring system 14. The lattice 4 may be made of a flexible material that transmits both power and data and may be constructed of an array of repeating geometric patterns. The size of lattice 4 may be determined by the limitations resulting from the relationship between the surface area to be monitored by the lattice 4 and the conductive, electrical, and physical properties of the lattice 4. Intersections 6 may be disposed at the junctions of lattice 4. The lattice 4 may be comprised of any desired repeating shape. For example and without limit, the lattice may be formed of repeating triangular, square, rectangular, circular, polygonal, and/or parallelogram shapes. In certain embodiments, the lattice may be formed and/or may comprise any other desired shape. The lattice may also be formed as, for example and without limitation, a mesh, net, screen, and/or web. The lattice 4 may be constructed and formed using the primary sensor 10 and at least one secondary sensor 12. The primary sensor 10 may be any type of sensor, including but not limited to temperature sensors, pressure sensors, motion sensors, light sensors, oxygen sensors, heart rate sensors, touch sensors, proximity sensors, gas sensors, acoustic sensors, chemical sensors, acceleration sensors, humidity sensors, moisture sensors, presence sensors, force sensors, and/or a combination thereof. Secondary sensors 12 may also be any type of sensor, including but not limited to temperature sensors, pressure sensors, motion sensors, light sensors, oxygen sensors, heart rate sensors, touch sensors, proximity sensors, gas sensors, acoustic sensors, chemical sensors, acceleration sensors, humidity sensors, moisture sensors, presence sensors, force sensors, and/or a combination thereof. A primary sensor 10 forms the layout and design of the lattice 4 and may be configured to integrate with one or more secondary sensors 12. For example, the one or more secondary sensors 12 may be disposed at any intersection 6 of the primary sensor 10 of the lattice 4. The entire lattice 4 may be electronically connected to a monitoring system 14 which may accept and process both power and data transmissions from the lattice 4. The monitoring system 14 may include any number of computers, processors, memories, databases, software modules, and/or other components, which may be utilized to analyze, process, store, and manipulate data received from the primary sensor 10 and/or secondary sensors 12. A series of lattices 4 may be connected to cover great distances or span massive surfaces. A series of connected lattices 4 may comprise a super lattice 18. The Super Modular Monitoring System 2 may support an alternating electric current, direct electric current, and/or any other electric current technology.

Figure 2:
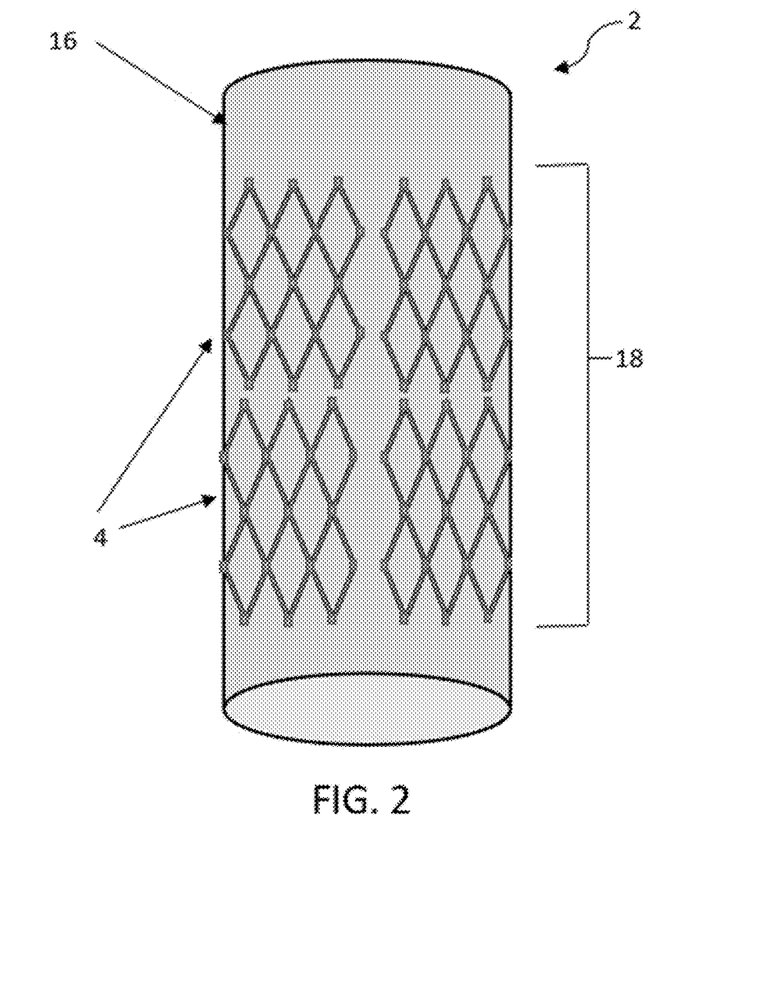
FIG. 2 is an overhead view of a Super Modular Monitoring System as deployed on a three-dimensional object. The Super Modular Monitoring System shown in FIG. 2 includes 4 lattices.

FIG. 2 shows four lattices 4 in operation. The lattices 4 may be deployed on a base object 16 that is being monitored and together form a super lattice 18. Although the base object 16 in FIG. 2 is shown as a pipe, it will be understood that the Super Modular Monitoring Systems may be used to monitor any object, such as a 3-dimensional object, or component of an object. For example, a Super Modular Monitoring System 2 could also be configured to monitor the status of a human body, building or building component, vehicle or vehicle component, ground surface, animal, tree, volcano, fault line, weapon, aircraft, railroad, road, bridge and other infrastructure, bicycle, and/or any other objects. The sensors of a Super Modular Monitoring System 2 may monitor for a variety of conditions, including strain, temperature, motion, position in space, flow, oxygen saturation, vascular lag, wall thickness, light, heart rate, touch, proximity, gases, sound, chemicals, acceleration, humidity, moisture, presence, force, etc, and/or a combination thereof. In certain embodiments, the primary sensors 10 and secondary sensors 12 may monitor for any condition capable of being monitored with sensors.

The primary sensor 10 may most often be the mode of connection to the base object 16 being monitored. The primary sensor 10 may be capable of measuring for a specific series of changes in the base object 16 that is being monitored. For example, the primary sensor 10 may be used to monitor changes in electrical resistance to determine Freedom and Constraint Topology ("FACT") on the surface of a base object 16, allowing the determination of changes in deflection, shearing force, and general motion with respect to the base object 16. As an example, the primary sensor 10 measures changes in voltage across the primary sensor 10 to determine a change in the length of base object 16 and/or motion of the base object 16. A 3D model may be built based on these measured changes in resistance. In certain embodiments, the primary sensor 10 may also be capable of powering and transmitting data for discrete secondary sensors 12 and may also be scalable. The size and shape of the primary sensor 10 may be utilized to determine the size and shape of the lattice 4. Because the primary sensor 10 may be comprised of an array of repeating geometric patterns, the lattice 4 and super lattice 18 structures may be constructed very quickly with known electrical and conductive properties. The repeating geometric patterns may include, but are not limited to, triangular, square, rectangular, circular, polygonal, parallelogram shapes, and/or any other desired shapes.

The secondary sensors 12 may be integrated into the primary sensor 10 to create a sensor-within-a-sensor platform. The secondary sensors 12 may measure specific metrics, including, for example, strain, temperature, motion, position in space, flow, oxygen saturation, vascular lag, wall thickness, light, heart rate, touch, proximity, gas, sound, chemicals, acceleration, humidity, moisture, presence, force, etc., and/or a combination thereof. One embodiment of secondary sensors 12 is conductive tabs 8. Conductive tabs 8 may be comprised of any conductive material. The conductive tabs 8 may measure any condition, including but not limited to strain, heat, motion, position in space, etc. or a combination thereof. The conductive tabs 8 may be preferably made of gold, however any other suitable material may be utilized. In certain embodiments, the secondary sensors 12 may not accept power and data over the same transmission lines of the lattice 4. In certain embodiments, the secondary sensors 12 may be configured to monitor for conditions that cannot be monitored by the primary sensor 10.

The Super Modular Monitoring System 2 may be modular in that each component part of the Super Modular Monitoring System 2 may be independently removed, changed, replaced, or repaired. For example, a section of primary sensor 10 may be removed from the main body of the primary sensor 10, secondary sensors 12 may be removed or replaced, sections of lattice 4 may be removed or replaced, and sections within a super lattice 18 may be removed or replaced. The Super Modular Monitoring System 2 may be configured to not lose functionality when components are removed regardless of the size of the system. Additionally, removing sensor components within a Super Modular Monitoring System 2 does not impede the flow of electricity or data. Also, in certain embodiments, because no portion of any layer within the Super Modular Monitoring System 2 is a closed loop, the Super Modular Monitoring System 2 may allow for new components to be integrated.

In use, the Super Modular Monitoring System 2 allows for the monitoring of 3-dimensional objects that may be complex in shape and/or massive in size or length. Any 3-dimensional shape may be tessellated, or covered in repeated geometric patterns of identical interlocking shapes, which allows the surface of a 3-dimensional object to be approximated in two dimensions. This approximates a 3-dimensional surface as 2-dimensional planes as the active monitoring area. For example, the surface area of a human arm may be approximated as the curved surface of a cylinder. The surface area may determine the geometric shape of the primary sensor 10 and the distance between secondary sensors 12. The relationship between 3-dimensional shape and surface area may determine the number of segments in a single cell, hence the number of repeating geometric cells over a given area. The approximated surface area of the 3-dimensional object determines the geometric shape of the lattice 4 and primary sensor 10 and the size and number of segments in a single lattice 4. The frequency of secondary sensor 12 placement may be also determined by the specific monitoring needs related to the base object 16. The geometric pattern may be utilized to determine the maximum number of secondary sensors 12 that may be integrated. In certain embodiments, the secondary sensors 12 may be placed at the intersections 6 between cell segments. In certain embodiments, the secondary sensors 12 may be placed at other locations of the lattice 4. The type of sensors embedded may be determined by use case—for example, pipeline monitoring may require monitoring acoustics to monitor flow while monitoring a human body may require a shirt that includes EKG pads for monitoring heart rate. The frequency of sensor placement may also be determined by use case—for example, oil pipelines may require thermal sensors placed every 10 feet while water pipes may only require thermal sensors every 100 feet.

In certain embodiments, the Super Modular Monitoring System 2 may monitor the metrics collected by both the primary sensors 10 and secondary sensors 12 on the same system clock at monitoring system 14. All of the data from the primary sensor 10 and secondary sensors 12 may be transmitted to the monitoring system 14 at the same time. This allows for less data processing at the monitoring system 14, which in turn provides faster data access and faster feedback regarding the monitoring of base object 16. Measurement collection that occurs simultaneously, on the same system clock allows excellent speed of access and feedback as well as opportunities for straightforward integration between signals. Thus, the present disclosure allows for sensor output that may be collated, analyzed as a time series by simple linear models, and used to build predictive models of events relevant to the monitored environment related injury or structural or catastrophic failure, for example. in certain embodiments, the data from the primary sensor 10 and the secondary sensors 12 may be configured to be transmitted to the monitoring system 14 at staggered times, at desired time intervals, at different times, and/or at any time. Because the Super Modular Monitoring System 2 is modular, it allows for the introduction of new secondary sensors 12 into the system as needed without redesigning the entire system or adding a new circuit to the system. If the size or portion of the base object 16 to be monitored changes, lattices 4 may be added or removed from the system as necessary. Existing commercial sensor components may be used as part of the Super Modular Monitoring System 2. For example, biometric sensors (movement, heart rate, blood oxygen saturation, etc.) and industrial sensors (strain, vibration, acoustic, etc.) may be used.

Figure 3:
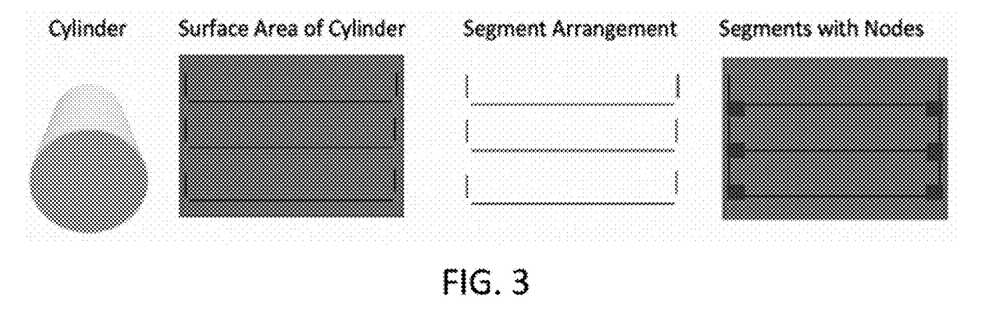
FIG. 3 is a sample lattice as disposed on a cylinder.

As shown in FIG. 3, sensor integration throughout the entire surface area of an object based on the shape of the primary sensor array may be characterized by the total surface area of the object being monitored and the specific sensor requirements dictated by the application. Ultimately, the technology provided by the present disclosure integrates sensors quickly and efficiently into a design without having to design a use-case specific circuit to accommodate those sensors. A pass-through may be connected to each node without a sensor, and may allow transmission of current and data between segments.

Signals reported by the present disclosure allow, in increasing order of complexity: (1) accurate monitoring of the desired shape as a time series, (2) complex instantaneous measurements by combining signals (for instance, measuring electrical to vascular lag as a proxy for vascular stiffness, or monitoring wall thickness and ambient temperature to determine the brittleness of a concrete section of bridge), the integration of (1) and (2) into near-instantaneous monitoring or user feedback, and the eventual acquisition of a sufficient database of integrated signals to form models for catastrophic events predicted in advance.

For example, with reference to FIG. 3, when the lattice 4 with intersections 6 is applied around a cylinder, it forms a parabolic 3-dimensional shape. As an example, the lattice 4 in this shape may be able to monitor multiple types of strain across multiple planes via a primary sensor 10, as well as temperature, flow and/or expansion via secondary sensors 12. As disclosed above, all measurements may be on the same system clock and the output may be sent to a common table.

Figure 4:
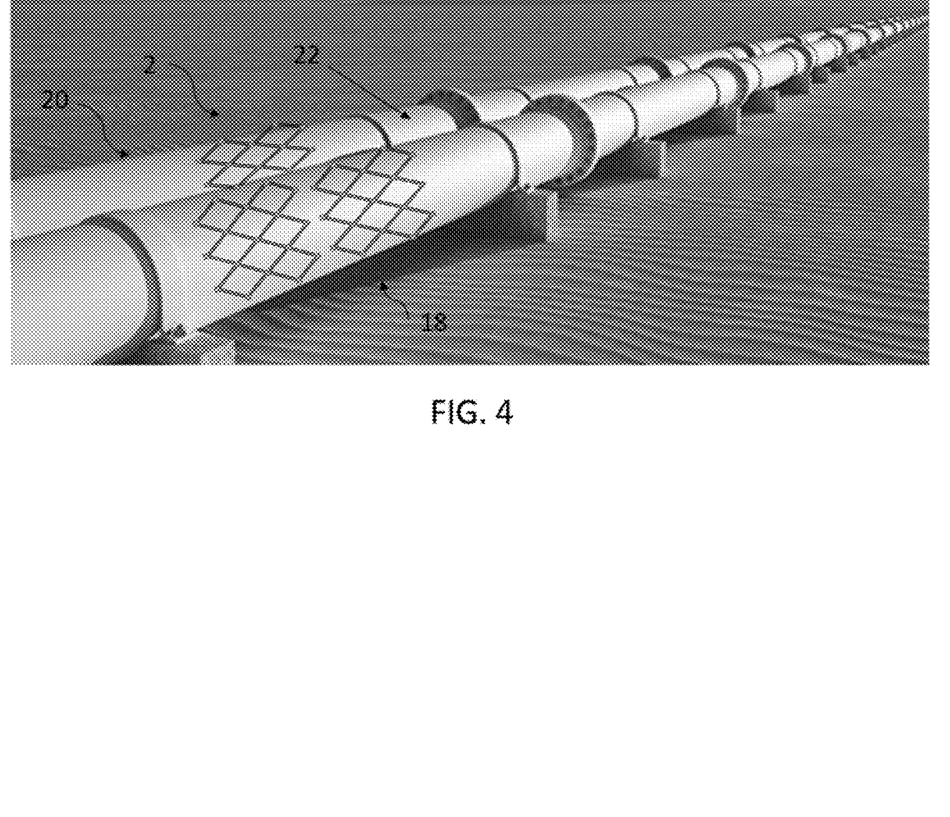
FIG. 4 is a view of one embodiment of the Super Modular Monitoring System wherein the system is used to monitor a pipeline.

In one embodiment shown in FIG. 4, a Super Modular Monitoring System 2 is used to monitor various aspects of an operational oil pipeline 20. Primary sensors 10 are provided that wrap around the cylindrical surface 22 of pipeline 20. Primary sensors 10 monitor a specified condition of the pipeline 20, for example and without limitation, primary sensors 10 may monitor the pipeline for changes in diameter, length, temperature, or a combination thereof. As many primary sensors 10 may be used to monitor any amount of the surface area of pipeline 20 deemed necessary. Additionally, secondary sensors 12 may be included within the lattice 4 of primary sensors 10 to monitor other conditions of the pipeline, including, for example and without limitation, movement, temperature, corrosion, or a combination thereof. The lattice 4 of primary sensors 10 and secondary sensors 12 may be incorporated into a sheet of material as necessary to protect the lattice 4 or allow for ease of installation. All of the conditions measured by primary sensors 10 and secondary sensors 12 may be reported to a monitoring system 14 at the same time and using the same system clock. In certain embodiments, the primary sensors 10 and secondary sensors 12 may transmit data to the monitoring system via the lattice 4 directly. Thus, a set of complete and accurate information selected to be monitored regarding pipeline 20 is available.

Figure 5:
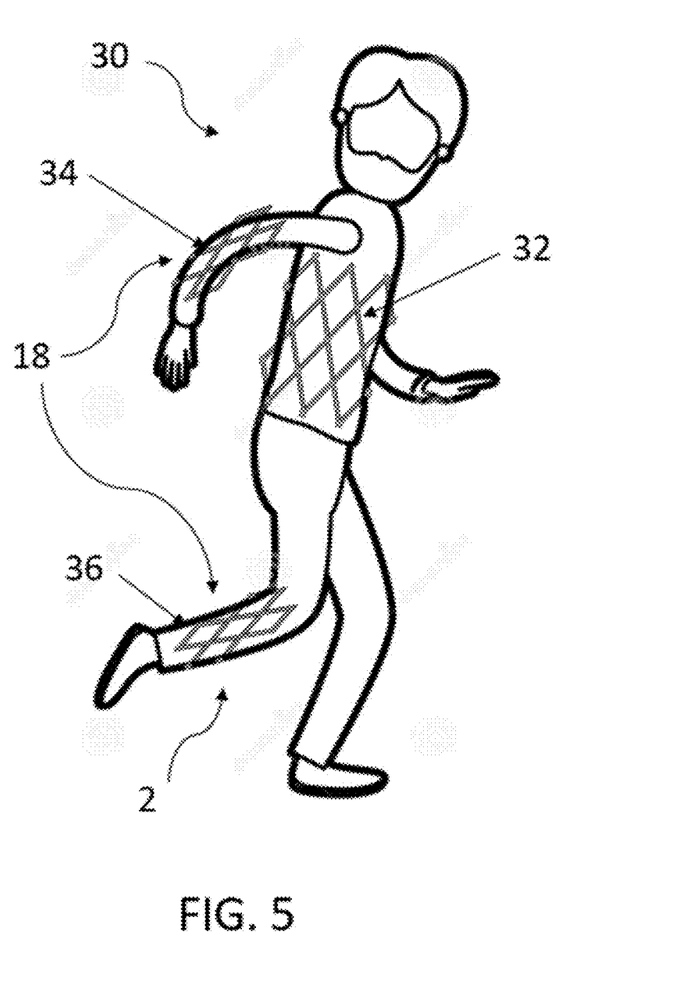
FIG. 5 is a view of one embodiment of the Super Modular Monitoring System wherein the system is used to monitor a human body.

In another embodiment shown in FIG. 5, a Super Modular Monitoring System 2 is used to monitor a human body 30. Primary sensors 10 are provided that wrap around selected parts of the body 30, for example the trunk 32 of the body 30, arms 34 of the body 30 and legs 36 of the body 30. The primary sensors 10 monitor a specified condition of body 30, for example and without limitation movement and temperature. As many primary sensors 10 may be used to monitor any amount of the surface area of body 30 deemed necessary. Additionally, secondary sensors 12 may be embedded into the lattice 4 of primary sensors 10 to monitor other conditions of the body 30, including, for example and without limitation, movement, temperature, and respiration. The lattice 4 of primary sensors 10 and secondary sensors 12 may be incorporated into a piece of clothing, for example and without limitation a shirt, pants, and/or bodysuit. All of the conditions measured by primary sensors 10 and secondary sensors 12 may be reported to a monitoring system 14 at the same time and using the same system clock. Thus, a set of complete and accurate information selected to be monitored regarding body 30 is available. Although two embodiments have been described in detail above, it will be understood that Super Modular Monitoring System 2 may be used to monitor conditions on any object. Objects that may be monitored include, but are not limited to, buildings and building components, vehicles and vehicle components, ground surfaces, animals, trees, volcanos, fault lines, weapons, aircrafts, railroads, roads, bridges and other infrastructure, bicycles, and other objects.

As described in the present disclosure, a super modular monitoring system is provided which includes a sensor-within-a-sensor configuration. The primary sensor is formed of a lattice. A secondary sensor may be provided at each intersection of the lattice. Any condition that may be measured using a sensor may be measured by the super modular monitoring system of the invention. More than one primary sensor may be used to cover more surface area as necessary and primary and secondary sensors may be removed, added, or replaced as necessary without re-wiring the super modular monitoring system. The super modular monitoring system may be used to monitor any three-dimensional object.

Figure 6:
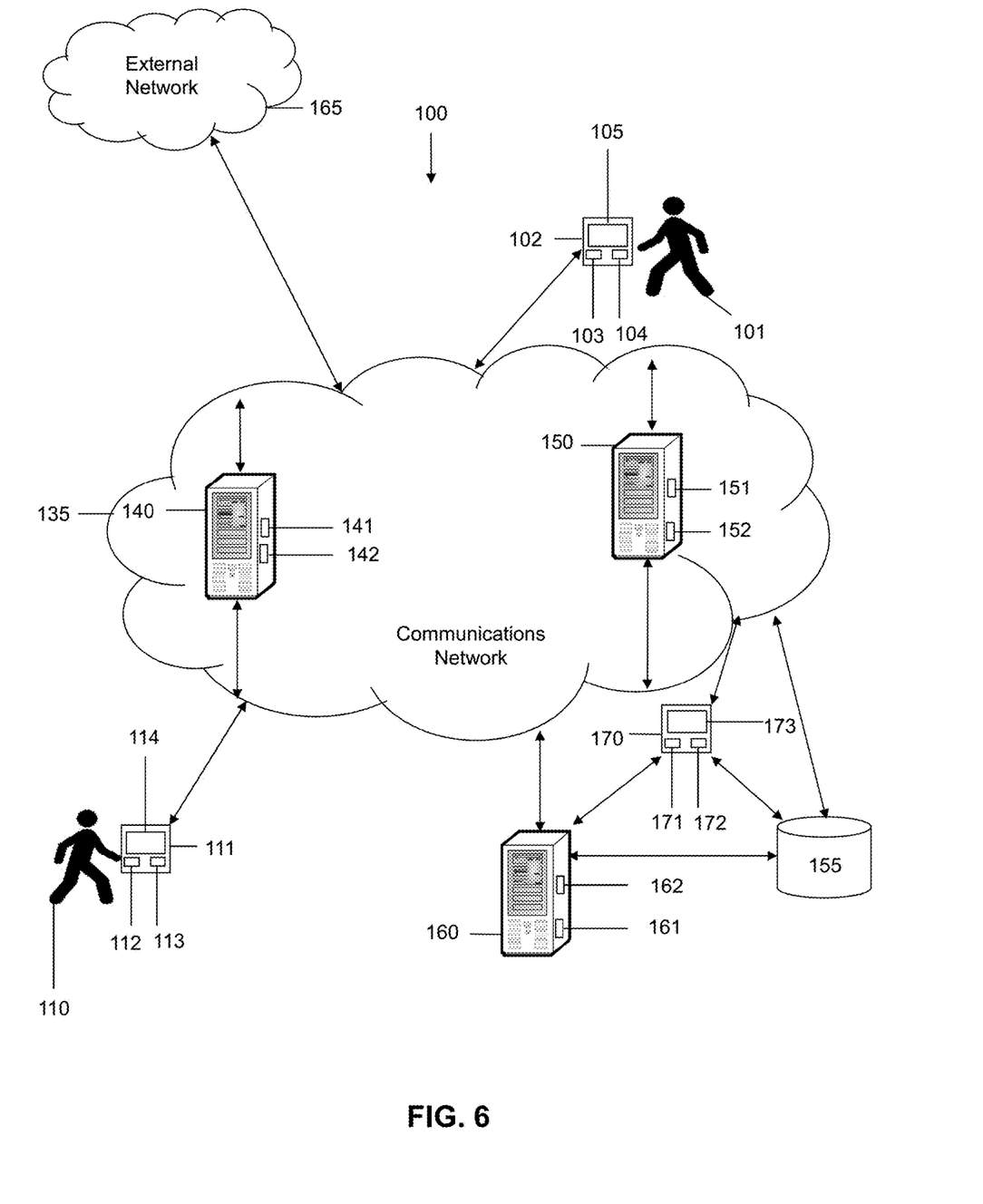
FIG. 6 is a schematic diagram of a system that may be utilized to facilitate the operative functioning of the Super Modular Monitoring System according to an embodiment of the present disclosure.

In certain embodiments, the Super Modular Monitoring System 2 may be configured to communicatively link with a system 100, as shown in FIG. 6. The system 100 may be configured to perform any of the functionality performed by the Super Modular Monitoring System 2 and/or operations offloaded by the Super Modular Monitoring System 2 to the system 100. For example, in certain instances, the computing, storage, and/or other resources of the Super Modular Monitoring System 2 may be overloaded or may be nearing a threshold level that warrants offloading operations and functionality to the system 100 to assist the Super Modular Monitoring System 2 in completing various operations and to increase performance of the Super Modular Monitoring System 2. Notably, any of the components of the Super Modular Monitoring System 2 may be configured to communicate with any of the components of the system 100, such as via a wired connection, wireless connection, any other type of connection, or a combination thereof. In certain embodiments, the system 100 may form a part of the monitoring system 14.

The system 100 may be configured to support, but is not limited to supporting, monitoring applications and services, sensor-based applications and services, wearable device applications and services, health monitoring applications and services, communication applications and services, alert applications and services, data and content services, data aggregation applications and services, big data technologies, data synthesis applications and services, data analysis applications and services, computing applications and services, cloud computing services, internet services, satellite services, telephone services, software as a service (SaaS) applications, mobile applications and services, and any other computing applications and services. The system may include a first user 101, who may utilize a first user device 102 to access data, content, and applications, or to perform a variety of other tasks and functions. In certain embodiments, the first user 101 may be a user that is a worker at oil pipeline or any other location that may wish to monitor conditions of an oil pipeline. In certain embodiments, the first user 101 may be a user that is seeking to monitoring various biological and/or health conditions of himself or herself, such as by utilizing the Super Modular Monitoring System 2. In certain embodiments, the first user 101 may be the individual illustrated in FIG. 5.

The first user device 102 utilized by the first user 101 may include a memory 103 that includes instructions, and a processor 104 that executes the instructions from the memory 103 to perform the various operations that are performed by the first user device 102. In certain embodiments, the processor 104 may be hardware, software, or a combination thereof. The first user device 102 may also include an interface 105 (e.g. screen, monitor, graphical user interface, audio device interface, etc.) that may enable the first user 101 to interact with various applications executing on the first user device 102, to interact with various applications executing within the system 100, and to interact with the system 100 itself. In certain embodiments, the first user device 102 may be a computer, a laptop, a tablet device, a phablet, a server, a mobile device, a smartphone, a smart watch, and/or any other type of computing device. Illustratively, the first user device 102 is shown as a mobile device in FIG. 1. The first user device 102 may also include a global positioning system (GPS), which may include a GPS receiver and any other necessary components for enabling GPS functionality, accelerometers, gyroscopes, sensors, and any other componentry suitable for a mobile device. In certain embodiments, the first user device 102 may be configured to include any number of sensors, such as, but not limited to, temperature sensors, pressure sensors, motion sensors, light sensors, oxygen sensors, heart rate sensors, touch sensors, proximity sensors, gas sensors, acoustic sensors, chemical sensors, acceleration sensors, humidity sensors, moisture sensors, presence sensors, force sensors, any type of sensors, or a combination thereof. In certain embodiments, the first user device 102 may be configured to communicate with any of the components of the Super Modular Monitoring System 2 and/or assist with any of the operations of the Super Modular Monitoring System 2.

In addition to the first user 101, the system 100 may include a second user 110, who may utilize a second user device 111 to access data, content, and applications, or to perform a variety of other tasks and functions. As with the first user 101, the second user 110 may be a user that is a worker at an oil pipeline or other industrial location. However, in certain embodiments, the second user 110 may be a supervisor of the first user 101, a colleague of the first user 101, and/or any other type of user. Much like the first user 101, the second user 110 may utilize second user device 111 to access an application (e.g. a browser or a mobile application) executing on the second user device 111 that may be utilized to access web pages, data, and content associated with the system 100. The second user device 111 may include a memory 112 that includes instructions, and a processor 113 that executes the instructions from the memory 112 to perform the various operations that are performed by the second user device 111. In certain embodiments, the processor 113 may be hardware, software, or a combination thereof. The second user device 111 may also include an interface 114 (e.g. a screen, a monitor, a graphical user interface, etc.) that may enable the second user 110 to interact with various applications executing on the second user device 111, to interact with various applications executing in the system 100, and to interact with the system 100. In certain embodiments, the second user device 111 may be a computer, a laptop, a tablet device, a phablet, a server, a mobile device, a smartphone, a smart watch, and/or any other type of computing device. Illustratively, the second user device 111 may be a computing device in FIG. 1. The second user device 111 may also include any of the componentry described for first user device 102. The second user device 111 may similarly be configured to communicate with any of the components of the Super Modular Monitoring System 2 and/or assist with any of the operations of the Super Modular Monitoring System 2.

In certain embodiments, the first user device 102 and the second user device 111 may have any number of software applications and/or application services stored and/or accessible thereon. For example, the first and second user devices 102, 111 may include applications for determining and analyzing conditions associated with monitored objects, determining and analyzing health conditions, applications for determining and analyzing the physiological status of a user, applications for generating alerts, applications for analyzing and interpreting sensor data, artificial intelligence applications, machine learning applications, big data applications, applications for analyzing data, applications for integrating data, cloud-based applications, search engine applications, natural language processing applications, database applications, algorithmic applications, phone-based applications, product-ordering applications, business applications, e-commerce applications, media streaming applications, content-based applications, database applications, gaming applications, internet-based applications, browser applications, mobile applications, service-based applications, productivity applications, video applications, music applications, social media applications, presentation applications, any other type of applications, any types of application services, or a combination thereof. In certain embodiments, the software applications and services may include one or more graphical user interfaces so as to enable the first and second users 101, 110 to readily interact with the software applications.

The software applications and services may also be utilized by the first and second users 101, 110 to interact with any device in the system 100, any components of the Super Modular Monitoring System 2, any network in the system 100, or any combination thereof. For example, the software applications executing on the first and second user devices 102, 111 may be applications for receiving data, applications for storing data, applications for analyzing sensor data, applications for determining health conditions, applications for determining how to respond to a health condition, applications for determining a physiological status of a user, applications for determining how to respond to an environmental condition (e.g. an environmental condition that may affect the first user 101), applications for receiving demographic and preference information, applications for transforming data, applications for executing mathematical algorithms, applications for generating and transmitting electronic messages, applications for generating and transmitting various types of content, any other type of applications, or a combination thereof. In certain embodiments, the first and second user devices 102, 111 may include associated telephone numbers, internet protocol addresses, device identities, or any other identifiers to uniquely identify the first and second user devices 102, 111 and/or the first and second users 101, 110. In certain embodiments, location information corresponding to the first and second user devices 102, 111 may be obtained based on the internet protocol addresses, by receiving a signal from the first and second user devices 102, 111, or based on profile information corresponding to the first and second user devices 102, 111.

The system 100 may also include a communications network 135. The communications network 135 of the system 100 may be configured to link each of the devices in the system 100 to one another. For example, the communications network 135 may be utilized by the first user device 102 to connect with other devices within or outside communications network 135. Additionally, the communications network 135 may be configured to transmit, generate, and receive any information and data traversing the system 100. In certain embodiments, the communications network 135 may include any number of servers, databases, or other componentry, and may be controlled by a service provider. The communications network 135 may also include and be connected to a cloud-computing network, a phone network, a wireless network, an Ethernet network, a satellite network, a broadband network, a cellular network, a private network, a cable network, the Internet, an internet protocol network, a content distribution network, any network, or any combination thereof. Illustratively, server 140 and server 150 are shown as being included within communications network 135.

Notably, the functionality of the system 100 may be supported and executed by using any combination of the servers 140, 150, and 160. The servers 140, and 150 may reside in communications network 135, however, in certain embodiments, the servers 140, 150 may reside outside communications network 135. The servers 140, and 150 may be utilized to perform the various operations and functions provided by the system 100, such as those requested by applications executing on the first and second user devices 102, 111. In certain embodiments, the server 140 may include a memory 141 that includes instructions, and a processor 142 that executes the instructions from the memory 141 to perform various operations that are performed by the server 140. The processor 142 may be hardware, software, or a combination thereof. Similarly, the server 150 may include a memory 151 that includes instructions, and a processor 152 that executes the instructions from the memory 151 to perform the various operations that are performed by the server 150. In certain embodiments, the servers 140, 150, and 160 may be network servers, routers, gateways, switches, media distribution hubs, signal transfer points, service control points, service switching points, firewalls, routers, edge devices, nodes, computers, mobile devices, or any other suitable computing device, or any combination thereof. In certain embodiments, the servers 140, 150 may be communicatively linked to the communications network 135, any network, any device in the system 100, or any combination thereof.

The database 155 of the system 100 may be utilized to store and relay information that traverses the system 100, cache information and/or content that traverses the system 100, store data about each of the devices in the system 100, and perform any other typical functions of a database. In certain embodiments, the database 155 may store the output from any operation performed by the system 100, operations performed and/or outputted by any component, program, process, device, network of the system 100 and/or Super Modular Monitoring System 2, or any combination thereof. For example, the database 155 may store data from data sources, such as, but not limited to, the primary sensor 10, the secondary sensors 12, the monitoring system 14, or a combination thereof. In certain embodiments, the database 155 may be connected to or reside within the communications network 135, any other network, or a combination thereof. In certain embodiments, the database 155 may serve as a central repository for any information associated with any of the devices and information associated with the system 100. Furthermore, the database 155 may include a processor and memory or be connected to a processor and memory to perform the various operations associated with the database 155. In certain embodiments, the database 155 may be connected to the servers 140, 150, 160, the first user device 102, the second user device 111, any devices in the system 100, any devices of the Super Modular Monitoring System 2, any other device, any network, or any combination thereof.

The database 155 may also store information obtained from the system 100, store information associated with the first and second users 101, 110, store location information for the first and second user devices 102, 111 and/or first and second users 101, 110, store user profiles associated with the first and second users 101, 110, store device profiles associated with any device in the system 100 and/or Super Modular Monitoring System 2, store communications traversing the system 100, store user preferences, store demographic information for the first and second users 101, 110, store information associated with any device or signal in the system 100, store information relating to usage of applications accessed by the first and second user devices 102, 111, store any information obtained from any of the networks in the system 100, store historical data associated with the first and second users 101, 110, store device characteristics, store information relating to any devices associated with the first and second users 101, 110, or any combination thereof. The database 155 may store algorithms for analyzing sensor data obtained from the primary sensors 10 and/or secondary sensors 12, algorithms for determining events, such as health conditions and/or physiological status, algorithms conducting artificial intelligence and/or machine learning, algorithms for comparing sensor data to baseline and/or threshold values, any other algorithms for performing any other calculations and/or operations in the system 100, or any combination thereof. The database 155 may also be configured to store information relating to detected events, actions to perform in response to the detected events, information indicating whether one or more of the actions have been performed, any other information provided by the system 100 and/or method 400, or any combination thereof. In certain embodiments, the database 155 may be configured to store any information generated and/or processed by the system 100, store any of the information disclosed for any of the operations and functions disclosed for the system 100 herewith, store any information traversing the system 100, or any combination thereof. Furthermore, the database 155 may be configured to process queries sent to it by any device in the system 100 and/or Super Modular Monitoring System 2.

The system 100 may also include an external network 165. The external network 165 of the system 100 may be configured to link each of the devices in the system 100 to one another. For example, the external network 165 may be utilized by the first user device 102, the second user device 111, and/or the Super Modular Monitoring System 2 to connect with other devices within or outside communications network 135. Additionally, the external network 165 may be configured to transmit, generate, and receive any information and data traversing the system 100. In certain embodiments, the external network 165 may include any number of servers, databases, or other componentry, and may be controlled by a service provider. The external network 165 may also include and be connected to a cloud-computing network, a phone network, a wireless network, an Ethernet network, a satellite network, a broadband network, a cellular network, a private network, a cable network, the Internet, an internet protocol network, a content distribution network, any network, or any combination thereof. In certain embodiments, the external network 165 may be outside the system 100 and may be configured to perform various functionality provided by the system 100, such as if the system 100 is overloaded and/or needs additional processing resources.

Notably, as shown in FIG. 1, the system 100 may perform any of the operative functions disclosed herein by utilizing the processing capabilities of server 160, the storage capacity of the database 155, or any other component of the system 100 to perform the operative functions disclosed herein. The server 160 may include one or more processors 162 that may be configured to process any of the various functions of the system 100. The processors 162 may be software, hardware, or a combination of hardware and software. Additionally, the server 160 may also include a memory 161, which stores instructions that the processors 162 may execute to perform various operations of the system 100. For example, the server 160 may assist in processing loads handled by the various devices in the system 100, such as, but not limited to, approximating the surface area of an object; determining an area of interest of the surface area of the object; providing a lattice formed of flexible conductive material to cover the area of interest;

connecting the lattice to a monitoring system 14; sensing conditions associated with the object by using the lattice; providing secondary sensors 12 at intersections of the lattice to monitor other conditions; transmitting the conditions to the monitoring system 14 for further analysis; analyzing the conditions to determine the impact of the conditions on the object and/or actions to be performed with respect to the object; and performing any other suitable operations conducted in the system 100 or otherwise. In one embodiment, multiple servers 160 may be utilized to process the functions of the system 100. The server 160 and other devices in the system 100, may utilize the database 155 for storing data about the devices in the system 100 or any other information that is associated with the system 100. In one embodiment, multiple databases 155 may be utilized to store data in the system 100.

In certain embodiments, the system 100 may also include a computing device 170. The computing device 170 may include one or more processors 172 that may be configured to process any of the various functions of the system 100. The processors 172 may be software, hardware, or a combination of hardware and software. Additionally, the computing device 170 may also include a memory 171, which stores instructions that the processors 172 may execute to perform various operations of the system 100. For example, the computing device 170 may assist in processing loads handled by the various devices in the system 100, such as, but not limited to, devices and components of the Super Modular Monitoring System 2.

Although the figures illustrate specific example configurations of the various components of the system 100, the system 100 may include any configuration of the components, which may include using a greater or lesser number of the components. For example, the system 100 is illustratively shown as including a first user device 102, a second user device 111, a database 125, a communications network 135, a server 140, a server 150, a server 160, a database 155, and an external network 165. However, the system 100 may include multiple first user devices 102, multiple second user devices 111, multiple databases 125, multiple communications networks 135, multiple servers 140, multiple servers 150, multiple servers 160, multiple databases 155, multiple external networks 165, and/or any number of any of the other components inside or outside the system 100. Similarly, the system 100 may include any number of data sources, applications, systems, and/or programs. Notably, any of the components of the system 100 may be integrated into the Super Modular Monitoring System 2. Furthermore, in certain embodiments, substantial portions of the functionality and operations of the system 100 may be performed by other networks and systems that may be connected to system 100.

Figure 7:
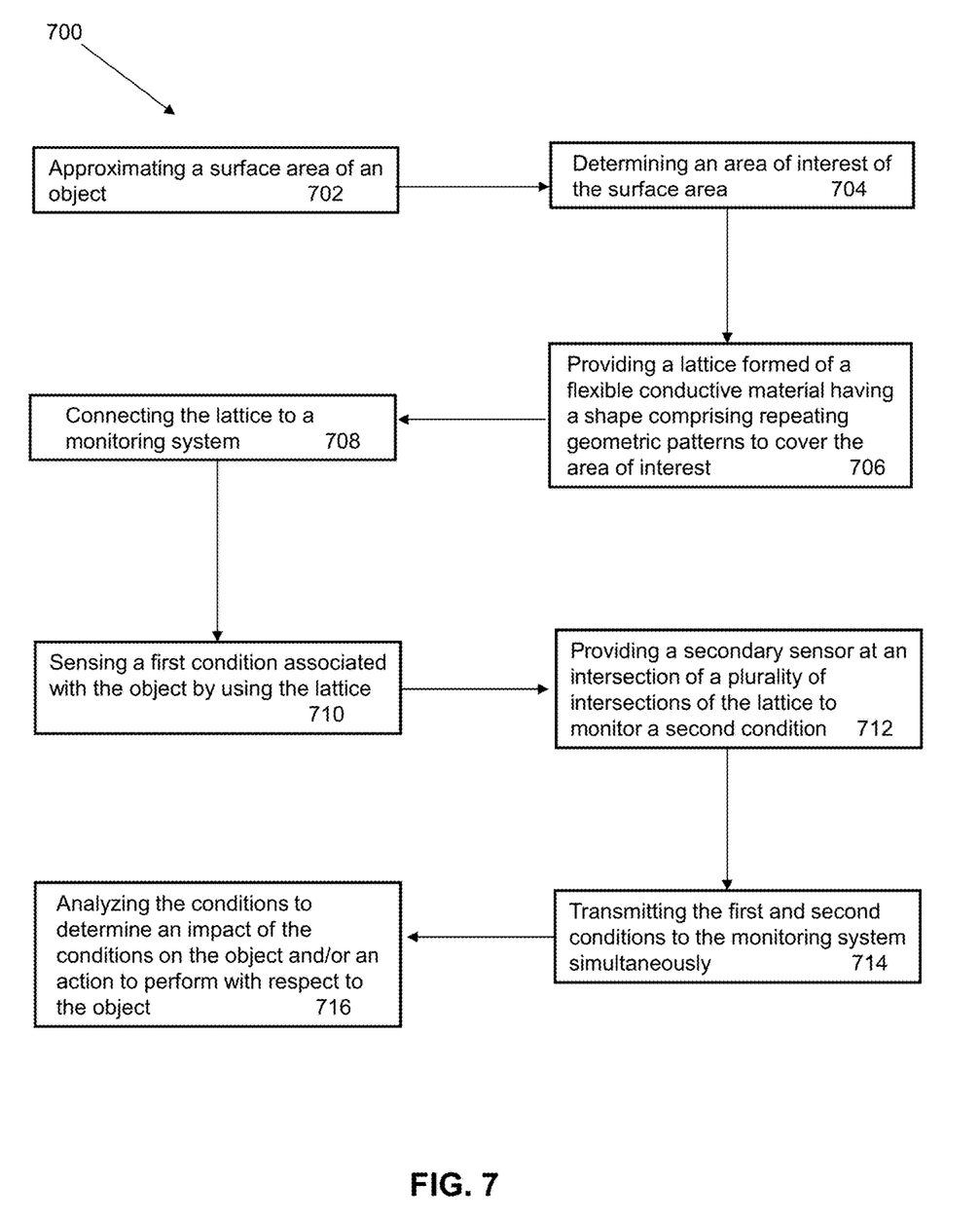
FIG. 7 is a flow diagram illustrating a sample method for utilizing a Super Module Monitoring System according to an embodiment of the present disclosure.

As shown in FIG. 7, an exemplary method 700 for providing and utilizing a Super Modular Monitoring System 2, is schematically illustrated. The method 700 may include, at step 702, approximating a surface area of an object. For example, the object may be a pipeline or even a user, such as first user 101 or second user 110. In certain embodiments, the approximating may be performed and/or facilitated by utilizing any of the components of the Super Modular Monitoring System 2, any of the components of the system 100, any other components, programs, and/or devices, or a combination thereof. At step 704, the method 700 may include determining an area of interest of the surface area of the object. In certain embodiments, the determining may be performed and/or facilitated by utilizing any of the components of the Super Modular Monitoring System 2, any of the components of the system 100, any other components, programs, and/or devices, or a combination thereof.

At step 706, the method 700 may include providing a lattice formed of a flexible conductive material. The lattice may have a shape comprising repeating geometric patterns and may be utilized to cover the area of interest of the object. For example, the lattice may be utilized to cover an oil pipeline or one or more body parts of a user. The conductive material of the lattice may be arranged in such a way so that the lattice has a plurality of intersections where various portions of the conductive material cross each other and/or meet to form the geometric patterns of the lattice. In certain embodiments, the providing of the lattice may be facilitated by utilizing any of the components of the Super Modular Monitoring System 2, any of the components of the system 100, any other components, programs, and/or devices, or a combination thereof. At step 708, the method 700 may include connecting the lattice to a monitoring system, such as monitoring system 14. In certain embodiments, the connecting may be performed and/or facilitated by utilizing any of the components of the Super Modular Monitoring System 2, any of the components of the system 100, any other components, programs, and/or devices, or a combination thereof.

At step 710, the method 700 may include sensing a first condition associated with the object by utilizing the lattice, which may serve as the primary sensor 10 of the Super Modular Monitoring System 2. The first condition, for example, may be any condition associated with the oil pipeline or the user—and/or even an environment associated with the oil pipeline and/or user. In certain embodiments, the sensing may be performed and/or facilitated by utilizing any of the components of the Super Modular Monitoring System 2, any of the components of the system 100, any other components, programs, and/or devices, or a combination thereof. At step 712, the method 700 may include providing a secondary sensor at an intersection of the plurality of intersections of the lattice to monitor a second condition and/or second conditions of the object being monitored. In certain embodiments, the providing of the secondary sensor may be facilitated by utilizing any of the components of the Super Modular Monitoring System 2, any of the components of the system 100, any other components, programs, and/or devices, or a combination thereof.

At step 714, the method 700 may include transmitting the first and/or second conditions obtained from the sensors to the monitoring system. In certain embodiments, the first and/or second conditions may be transmitted to the monitoring system at the same time. In certain embodiments, the transmitting may be performed and/or facilitated by utilizing any of the components of the Super Modular Monitoring System 2, any of the components of the system 100, any other components, programs, and/or devices, or a combination thereof. At step 716, the method 700 may include analyzing the first and/or second conditions to determine an impact of the conditions on the object and/or one or more actions to perform with respect to the object. For example, if the conditions indicate that the oil pipeline is expanding too rapidly based on the sensor data, an action to be performed may be to shut down the pipeline and send a person out to inspect the portion of the oil pipeline. As another example, if the conditions indicate that the user is breathing too heavily, the action to be performed may be that the user needs to stop what they are doing and measure other vital signs and/or contact a health provider. In certain embodiments, the analyzing of the conditions and/or the determining of the impact and actions may be performed and/or facilitated by utilizing any of the components of the Super Modular Monitoring System 2, any of the components of the system 100, any other components, programs, and/or devices, or a combination thereof. Notably, any of the functionality of the system 100, the Super Modular Monitoring System 2, or both may be incorporated in to the method 700 or vice versa.

Figure 8:
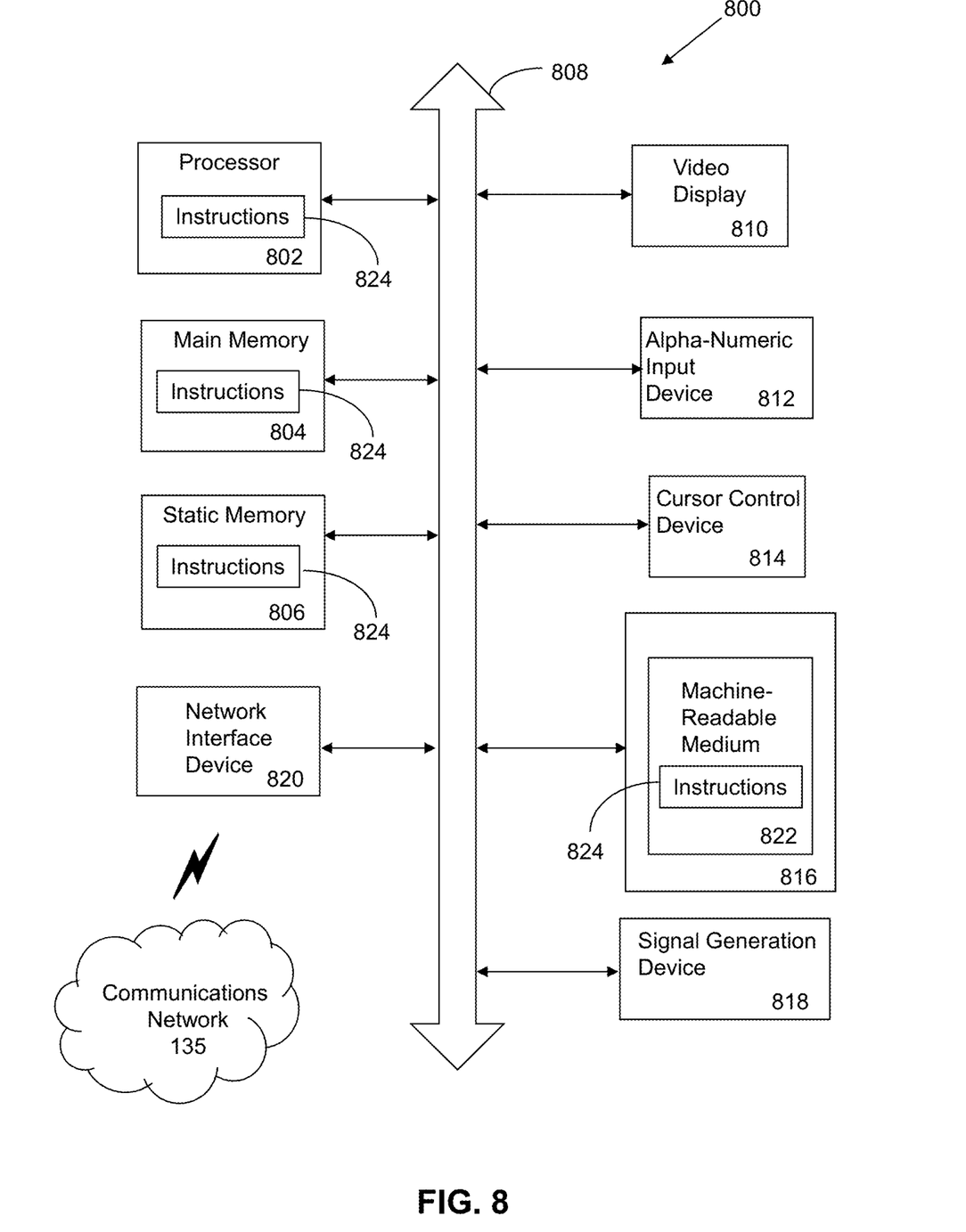
FIG. 8 is a schematic diagram of a machine in the form of a computer system within which a set of instructions, when executed, may cause the machine to perform any one or more of the methodologies or operations of the Super Modular Monitoring System.

Referring now also to FIG. 8, at least a portion of the methodologies and techniques described with respect to the exemplary embodiments of the system 100 can incorporate a machine, such as, but not limited to, computer system 500, or other computing device within which a set of instructions, when executed, may cause the machine to perform any one or more of the methodologies or functions discussed above. The machine may be configured to facilitate various operations conducted by the system 100. For example, the machine may be configured to, but is not limited to, assist the system 100 by providing processing power to assist with processing loads experienced in the system 100, by providing storage capacity for storing instructions or data traversing the system 100, or by assisting with any other operations conducted by or within the system 100.

In some embodiments, the machine may operate as a standalone device. In some embodiments, the machine may be connected (e.g., using communications network 135, another network, or a combination thereof) to and assist with operations performed by other machines, programs, functions, and systems, such as, but not limited to, the first user device 102, the second user device 111, the server 140, the server 150, the database 155, the server 160, the external network 165, the communications network 135, any device, system, and/or program, or any combination thereof. The machine may be connected with any component in the system 100. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 800 may include a processor 802 (e.g., a central processing unit (CPU), a graphics processing unit (GPU, or both), a main memory 804 and a static memory 806, which communicate with each other via a bus 808. The computer system 800 may further include a video display unit 810, which may be, but is not limited to, a liquid crystal display (LCD), a flat panel, a solid state display, or a cathode ray tube (CRT). The computer system 800 may include an input device 812, such as, but not limited to, a keyboard, a cursor control device 814, such as, but not limited to, a mouse, a disk drive unit 816, a signal generation device 818, such as, but not limited to, a speaker or remote control, and a network interface device 820.

The disk drive unit 816 may include a machine-readable medium 822 on which is stored one or more sets of instructions 824, such as, but not limited to, software embodying any one or more of the methodologies or functions described herein, including those methods illustrated above. The instructions 824 may also reside, completely or at least partially, within the main memory 804, the static memory 806, or within the processor 802, or a combination thereof, during execution thereof by the computer system 800. The main memory 804 and the processor 802 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine-readable medium 822 containing instructions 824 so that a device connected to the communications network 135, the external network 165, another network, or a combination thereof, can send or receive voice, video or data, and communicate over the communications network 135, the external network 165, another network, or a combination thereof, using the instructions. The instructions 824 may further be transmitted or received over the communications network 135, the external network 165, another network, or a combination thereof, via the network interface device 820.

While the machine-readable medium 822 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

The invention claimed is:

1. A method for monitoring an object with a sensor-within-a-sensor system comprising:
    approximating a surface area of the object;
    determining an area of interest upon the surface area;
    providing a lattice formed of a flexible conductive material having a shape of repeating geometric patterns to cover the area of interest, wherein the lattice has a plurality of intersections and is capable of conducting power and data signals;
    connecting the lattice to a monitoring system, the monitoring system configured to receive the power and data signals;
    sensing a first condition associated with the object by using the lattice;
    providing a secondary sensor at an intersection of the plurality of intersections of the lattice, wherein the secondary sensor monitors a second condition;
    transmitting the first and the second conditions to the monitoring system at a same time; and
    removing the secondary sensor and replacing it with a replacement secondary sensor.

2. The method of claim 1 wherein a plurality of lattices are provided to monitor the area of interest.

3. The method of claim 1, further comprising removing the lattice and replacing it with a replacement lattice.

4. The method of claim 1, further comprising sensing a first condition using the lattice by monitoring a voltage in the lattice.

5. A method for monitoring an object with a sensor-within-a-sensor system comprising:
    approximating a surface area of the object;
    determining an area of interest upon the surface area;
    providing a lattice formed of a flexible conductive material having a shape of repeating geometric patterns to cover the area of interest, wherein the lattice has a plurality of intersections and is capable of conducting power and data signals;
    connecting the lattice to a monitoring system, the monitoring system configured to receive the power and data signals;
    sensing a first condition associated with the object by using the lattice;
    providing a secondary sensor at an intersection of the plurality of intersections of the lattice, wherein the secondary sensor monitors a second condition;
    transmitting the first and the second conditions to the monitoring system at a same time; and
    removing the lattice and replacing it with a replacement lattice.

6. The method of claim 5 wherein a plurality of lattices are provided to monitor the area of interest.

7. The method of claim 5, further comprising sensing a first condition using the lattice by monitoring a voltage in the lattice.

8. A system for monitoring an object comprising:
    a lattice formed of a flexible conductive material having a shape of repeating geometric patterns and configured to cover an area of interest of the object to approximate a surface area of the object, the lattice having a plurality of intersections and capable of conducting power and data signals, a secondary sensor included at an intersection of the plurality of intersections of the lattice;
    a monitoring system that is connected to the lattice and configured to receive the power and data signals;
    the lattice configured to sense a first condition associated with the object, the secondary sensor configured to monitor a second condition, and the lattice configured to transmit the first and second conditions to the monitoring system at a same time; and
    the secondary sensor being removable and replaceable with a replacement secondary sensor.

9. The system of claim 8, wherein a plurality of secondary sensors are positioned at a plurality of intersections.

10. The system of claim 9 wherein the secondary sensors are primarily formed of gold foil.

11. The system of claim 8, wherein the object is an oil pipeline.

12. The system of claim 8, wherein the object is a human body.

* * * * *